US00PP22421P2

(12) United States Plant Patent
Perkins

(10) Patent No.: US PP22,421 P2
(45) Date of Patent: Dec. 27, 2011

(54) ***ANGELONIA* PLANT NAMED 'CAS RASPRY'**

(50) Latin Name: *Angelonia angustifolia*
Varietal Denomination: Cas Raspry

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/806,926

(22) Filed: Aug. 24, 2010

(51) Int. Cl.
*A01H 5/00* (2006.01)

(52) U.S. Cl. ..... Plt./404

(58) Field of Classification Search ..... Plt./404
See application file for complete search history.

*Primary Examiner* — Annette Para
(74) *Attorney, Agent, or Firm* — S. Matthew Edwards

(57) ABSTRACT

A new *Angelonia* plant named 'Cas Raspry' particularly distinguished by the large bold red-purple flowers; medium green foliage; with a compact and decumbent, well-branched plant habit.

1 Drawing Sheet

Latin name of the genus and species of the plant claimed: *Angelonia angustifolia.*

Varietal denomination: 'Cas Raspry'.

BACKGROUND OF THE NEW PLANT

The present invention comprises a new *Angelonia,* botanically known as *Angelonia angustifolia,* and hereinafter referred to by the variety name 'Cas Raspry'.

'Cas Raspry' is a product of a planned breeding program. The new cultivar 'Cas Raspry' has large bold red-purple flowers; medium green foliage; with a compact and decumbent, well-branched plant habit.

'Cas Raspry' originated from a hybridization made in August 2006 in a controlled breeding program in Gilroy, Calif. The female parent was an unpatented proprietary plant identified as '655-1' with rose-purple flower color. '655-1' has lighter green foliage and a less compact habit than 'Cas Raspry'.

The male parent of 'Cas Raspry' was an unpatented, proprietary plant identified as '623-1' with deep pink flower color. '623-1' has lighter green foliage and is less floriferous than 'Cas Raspry'. The resultant seed was sown in May 2007.

'Cas Raspry' was selected as one flowering plant within the progeny of the stated cross in September 2007 in a controlled environment in Gilroy, Calif.

The first act of asexual reproduction of 'Cas Raspry' was accomplished when vegetative cuttings were propagated from the initial selection in the September 2007 in a controlled environment in Gilroy, Calif.

BRIEF SUMMARY OF INVENTION

Horticultural examination of plants grown from cuttings of the plant initiated in September 2007 in Gilroy, Calif., and continuing thereafter, has demonstrated that the combination of characteristics as herein disclosed for 'Cas Raspry' are firmly fixed and are retained through successive generations of asexual reproduction.

'Cas Raspry' has not been observed under all possible environmental conditions. The phenotype may vary significantly with variations in environment such as temperature, light intensity and day length.

A Plant Breeder's Right for this cultivar was applied for in Canada on Feb. 25, 2010 (#10-6864). 'Cas Raspry' has not been made publicly available more than one year prior to the filing of this application.

The following traits have been repeatedly observed and are determined to be basic characteristics of the new variety. The combination of these characteristics distinguishes this *Angelonia* as a new and distinct variety.

BRIEF DESCRIPTION OF THE PHOTOGRAPH

The accompanying photographic drawing shows typical flower and foliage characteristics of 'Cas Raspry' with colors being as true as possible with an illustration of this type. The photographic drawing shows 3 flowering potted plants of the new variety growing in an 8 inch basket and a close-up of the flowers. These photographs were taken in Gilroy, Calif. in April 2010 and were approximately 14 weeks of age.

DETAILED BOTANICAL DESCRIPTION

The plant descriptions, observations and measurements were taken in Gilroy, California in mid August 2010 on plants that were growing in 4 inch pots in a greenhouse. These plants were approximately 9 weeks of age.

Color Chart used: Royal Horticultural Society Colour Chart (R.H.S.) 2001

TABLE 1

DIFFERENCES BETWEEN THE NEW VARIETY 'CAS RASPRY' AND A SIMILAR VARIETY

| | 'Cas Raspry' | 'Cartbas Depink' (U.S. Plant Pat. No. 16,655) |
|---|---|---|
| Flower color: | RHS 67B to RHS 67C | RHS 67A |
| Stem length: | Shorter | Longer |
| Plant habit: | More compact | More upright |
| Sepal color: | RHS 141A to RHS 141B | RHS 144A with anthocyanins |

Plant:

*Form, growth and habit.*—Compact and decumbent, well-branched plant habit.

*Plant height.*—About 9.0 cm.
*Plant height* (*inflorescence included*).—About 9-13 cm.
*Plant width.*—45-50 cm.

Foliage:
*Immature, leaf color, upper surface.*—RHS 137A but a little darker.
*Lower surface.*—RHS 137B.
*Mature, leaf color, upper surface.*—RHS 137A but a little darker.
*Lower surface.*—RHS 137B.
*Length.*—5.2-5.8 cm.
*Width.*—1.1-1.2 cm.
*Shape.*—Narrowly elliptical.
*Base shape.*—Cuneate.
*Apex shape.*—Acute.
*Margin.*—Serrulate.
*Texture.*—Few glandular hairs on margins.
*Color of veins, upper surface.*—RHS 146B.
*Color of veins, lower surface.*—RHS 146B.

Stem:
*Number of main stems per plant.*—8.
*Color of stem.*—RHS 146B to RHS 146 C.
*Length of stem.*—2-15 cm.
*Diameter.*—0.2-0.25 cm.
*Length of internodes.*—1.8-2.0 cm.
*Texture.*—Glandular hairs.

Inflorescence:
*Type.*—Terminal raceme; florets, solitary in leaf axis (sometimes 2 or 3).
*Number of florets per raceme.*—20-24.
*Raceme color.*—RHS 146B to RHS 146C but sometimes has RHS 199B but lighter hues on the upper side.
*Raceme length.*—12-14 cm.
*Color of pedicel.*—RHS 146B overlaid with anthocyanins of about RHS 178B in varying hues.
*Length of pedicel.*—0.7-1.0 cm.
*Diameter of pedicel.*—0.075 cm.
*Texture.*—Glandular hairs.

Corolla:
*Form.*—Single, two-lipped (5 petaled, fused at base).
*Length of floret.*—2.0-2.2 cm.
*Width of floret.*—2.1-2.2 cm.
*Color upper lip petals, upper surface.*—RHS 67B to RHS 67C.
*Color upper lip petals, lower surface.*—RHS 67C but more grey.
*Size upper lip petal length.*—0.7 cm from corolla opening.
*Size upper lip petal width.*—1.0-1.1 cm.
*Color lower lip, laterial petals, upper surfaces.*—RHS 67B to RHS 67C.
*Color lower lip, lateral petals, lower surface.*—RHS 67C but more grey.
*Size lower lip, lateral petals length.*—0.7 cm from corolla opening.
*Size lower lip, lateral petals width.*—0.9-1.0 cm.
*Color lower lip, mid-petal, upper surface.*—RHS 67B to RHS 67C with slightly darker blotches basally.
*Color lower lip, mid- petal, lower surface.*—RHS 67C but more grey.
*Size lower lip, mid- petal length.*—0.8 cm from corolla opening.
*Size lower lip, mid- petal width.*—0.6-0.7 cm.
*Petal shape.*—Obovate.
*Apex shape.*—Obtuse to rounded.
*Margin.*—Entire.
*Petal texture.*—Papillose.
*Corolla color, inside.*—RHS 155D ground color overlaid with RHS 59A blotches that bleed into the ground color.
*Corolla color, outside.*—RHS 157B to RHS 157C ground color overlaid with blotches of RHS 59A but a little deeper.
*Duration of flowering.*—Continuous flowering throughout the Summer.
*Fragrance.*—None.
*Lastingness of individual florets.*—About 6-7 days depending on temperatures and lighting.

Bud (when color starts to show):
*Color.*—RHS 155C with RHS 51B to RHS 51D overlay.
*Length.*—0.7-0.8 cm.
*Width.*—0.5 cm.
*Shape.*—Orbicular.
*Number of sepals.*—5 fused at base.
*Color of sepals.*—RHS 141A to RHS 141B.
*Length of sepals.*—0.15-0.25 cm.
*Width of sepals.*—0.15-0.2 cm.
*Sepal shape.*—Lanceolate.
*Apex shape.*—Acute.
*Margins.*—Entire.
*Texture.*—Glandular hairs on both surfaces.

Reproductive organs:
*Pistil.*—1.
*Length.*—0.3 cm.
*Style color.*—RHS 145C.
*Stigma color.*—RHS 145C.
*Number of stamens.*—4, in pairs.
*Length filaments.*—0.3 cm.
*Color of filaments.*—RHS 155C.
*Color of pollen.*—Not observed.
*Pollen amount.*—Not observed.
*Fertility/seed set.*—Has not been observed.
*Disease /pest resistence.*—Has not been observed.

What is claimed is:

1. A new and distinct variety of *Angelonia* plant named 'Cas Raspry' substantially as illustrated and described herein.

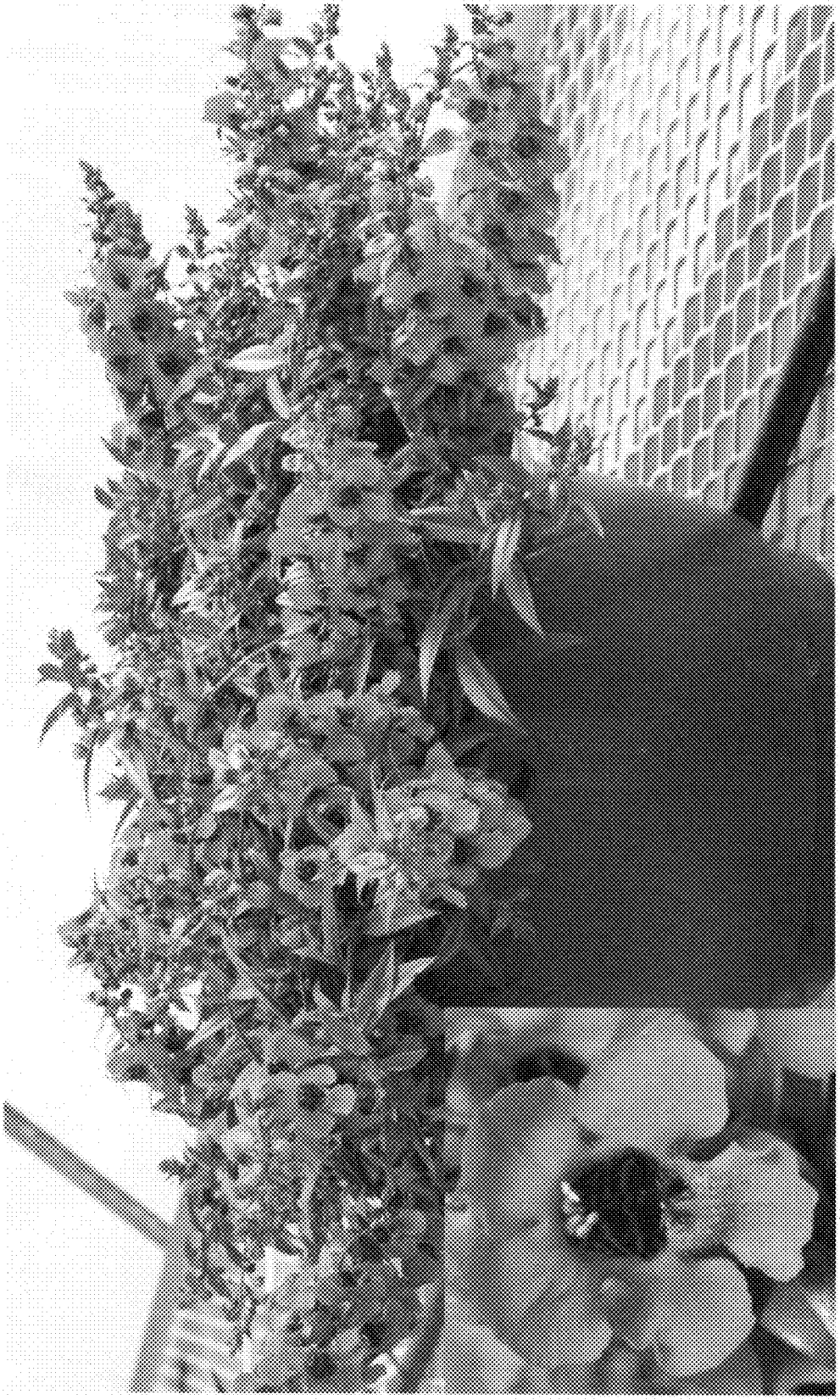

* * * * *